(12) United States Patent
Hsu et al.

(10) Patent No.: US 10,639,292 B2
(45) Date of Patent: *May 5, 2020

(54) METHOD OF TREATING HYPERGLYCEMIA

(71) Applicant: Center Laboratories, Inc., Taipei (TW)

(72) Inventors: Jui-Pao Hsu, Taipei (TW);
Guang-Tzuu Shane, Taipei (TW);
Meng-Ju Lee, Taipei (TW); Yi-Ping Liao, Taipei (TW); Yu-Yin Yeh, Taipei (TW); Shu-Hsien Chang, Taipei (TW)

(73) Assignee: CENTER LABORATORIES, INC., Taipei (TW)

( * ) Notice: Subject to any disclaimer, the term of this patent is extended or adjusted under 35 U.S.C. 154(b) by 7 days.

This patent is subject to a terminal disclaimer.

(21) Appl. No.: 16/179,896

(22) Filed: Nov. 3, 2018

(65) Prior Publication Data

US 2019/0321326 A1  Oct. 24, 2019

Related U.S. Application Data

(63) Continuation-in-part of application No. 15/957,956, filed on Apr. 20, 2018, now Pat. No. 10,278,943.

(51) Int. Cl.
*A61K 31/277* (2006.01)
*A61K 31/702* (2006.01)
*A61P 3/10* (2006.01)

(52) U.S. Cl.
CPC .......... *A61K 31/277* (2013.01); *A61K 31/702* (2013.01); *A61P 3/10* (2018.01)

(58) Field of Classification Search
CPC .................................................. A61K 31/277
See application file for complete search history.

(56) References Cited

U.S. PATENT DOCUMENTS

| 9,980,935 | B2 | 5/2018 | Hsu et al. |
| 2013/0210911 | A1 | 8/2013 | Lee et al. |

FOREIGN PATENT DOCUMENTS

| EP | 2573088 A1 | 3/2013 |
| WO | WO2010138535 A1 | 12/2010 |
| WO | WO2011057471 A1 | 5/2011 |
| WO | WO2011060255 A1 | 5/2011 |
| WO | WO2017198177 A | 11/2017 |

OTHER PUBLICATIONS

Sharma et al., Managing hypertension in diabetic patients—focus on trandolapril/verapamil combination, 2007, Vascular Health and Risk Management, 3(4), pp. 453-465 (Year: 2007).*
Campbell et al., Acarbose: It's Role in the Treatment of Diabetes Mellitus, 1996, The Annals of Pharmacotherapy, vol. 30, pp. 1255-1261 (Year: 1996).*
American Diabetes Association, Treatment of Hypertension in Adults with Diabetes, 2003, Diabetes Care, vol. 26, Suppl.1, pp. S80-S82 (Year: 2003).*
Dabhi et al., Voglibose: An Alpha Glucosidase Inhibitor, 2013, Journal of Clinical and Diagnostic Research, vol. 7(12), pp. 3023-3027 (Year: 2013).*
FDA Drug Description Label, COVERA-HS (verapamil hydrochloride) Extended-Release Tablets Controlled-Onset, 2011, pp. 1-17 (Year: 2011).*
Röjdmark et al, "Influence of Verapamil on Human Glucose Tolerance", The American Journal of Cardiology, vol. 57, Issue 7, Feb. 26, 1986, pp. D39-D43.
Sharma et al, "Managing hypertension in diabetic patients—focus on trandolaprillverapamil combination", Sep. 15, 2007 vol. 2007:3(4) pp. 453-465, Dovepress.
"Medication for type 2 diabetes", Aug. 27, 2008, IQWig.

* cited by examiner

*Primary Examiner* — Jeffrey S Lundgren
*Assistant Examiner* — Tori Strong

(57) ABSTRACT

Disclosed herein are methods for treating conditions and/or disorders related to hyperglycemia. Such conditions and/or disorders related to hyperglycemia include, but are not limited to, type I, II diabetes mellitus, gestational diabetes, other forms diabetes, and disorders related thereto. In particular, the present invention relates to methods of using (R)-(+)-verapamil or a pharmaceutically acceptable salt thereof and an α-glycosidase inhibitor in the treatment of conditions and/or disorders related to hyperglycemia.

8 Claims, 2 Drawing Sheets

METHOD OF TREATING HYPERGLYCEMIA

CROSS-REFERENCES TO RELATED APPLICATIONS

This application is a continuation-in-part application of U.S. application Ser. No. 15/957,956 filed Apr. 20, 2018, which is a continuation application of U.S. application Ser. No. 15/597,200 filed May 17, 2017, which claims the benefit of U.S. Provisional Application Ser. No. 62/339,131 filed May 20, 2016; the contents of the related applications are incorporated herein by reference.

BACKGROUND OF THE INVENTION

1. Field of the Invention

The present disclosure is generally directed to methods of treating hyperglycemia, such as diabetes mellitus, with a combination of (R)-(+)-verapamil or a pharmaceutically acceptable salt thereof, and an α-glycosidase inhibitor.

2. Description of Related Art

Diabetes mellitus is a condition in which a person's body does not produce enough, or does not properly respond to, insulin. Insulin is a hormone produced in the pancreas that enables cells to absorb glucose to turn it into energy. When insulin production is insufficient or when the body does not properly respond to insulin, glucose accumulates in the blood, which can lead to various complications. While there are several forms of diabetes, three forms are the most recognized: type I diabetes, type II diabetes, and gestational diabetes. Additionally, prediabetes is recognized s preceding diabetes and exists when blood glucose levels that are higher than normal but not yet high enough to be diagnosed as diabetes.

Type I diabetes or insulin-dependent diabetes mellitus (IDDM) is a metabolic disorder caused by destruction of the insulin-producing beta cells in the pancreas, which leads to insulin deficiency and high levels of glucose in plasma. The onset of type I diabetes generally results from an autoimmune etiology; however, idiopathic causes of beta cell destruction can occur for type I. Type 1 diabetes can affect children or adults, but was traditionally termed "juvenile diabetes" because it represents a majority of the diabetes cases in children.

Type II diabetes or non-insulin-dependent diabetes mellitus (NIDDM) has been found to possess inheritable aspects which can be greatly impacted by external environmental factors. The underlying etiologies of type II diabetes include deficiencies in insulin-producing beta cells; altered response to insulin by muscle, adipose, and liver cells; and abnormalities in the regulating mechanisms responsible for controlling carbohydrate and lipid metabolism following ingestion of food. Modulation in insulin-sensitivity is affected by environmental factors and behaviors, mostly a sedentary lifestyle and obesity. The cellular mechanisms that contribute to modulation of muscle and adipose cell sensitivity to insulin are complex and are not well understood. It is believed that altering insulin signaling pathways, increasing the amount of intracellular fat, and elevating levels of free fatty acids and other adipose tissue products can impact insulin-sensitivity.

Gestational diabetes occurs in pregnant women who have not previously been diagnosed with diabetes but who have high glucose levels during pregnancy. Gestational diabetes affects about 4% of all pregnant women and may precede development of type II diabetes.

If not properly controlled or stabilized, a hyperglycemic state has been associated with comorbidities including cardiovascular disease, vision impairment, various forms of neuropathy and cognitive impairment, stroke, and peripheral vascular disease. The common therapeutic approach, in addition to major modifications in an individual's dietary nutrition and physical activity, includes the use of anti-hyperglycemic drugs and insulin. Since the disease is chronic and progressive, and so far no treatment is able to reverse the progression, and thus there remains in this field a need of an improved medicament for treating conditions, diseases and/or disorders associated with hyperglycemia.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present invention relates to a medicament, which effectively reduces the blood glucose level of a hyperglycemia subject. The present invention therefore is useful for treating conditions related to hyperglycemia, which includes, but is not limited to, type I, type II diabetes mellitus, gestational diabetes, other forms of diabetes and/or disorders related thereto.

Accordingly, one aspect of the present disclosure relates to the combined use of (R)-(+)-verapamil or a pharmaceutically acceptable salt thereof and an α-glycosidase inhibitor for the manufacture of a pharmaceutical composition for the treatment of conditions related to type I, type II diabetes mellitus, gestational diabetes, other forms of diabetes and/or disorders related thereto.

The pharmaceutical composition of the present disclosure comprises (R)-(+)-verapamil or a pharmaceutically acceptable salt thereof, an α-glycosidase inhibitor, and a pharmaceutically acceptable excipient.

According to preferred embodiments of the present disclosure, the (R)-(+)-verapamil or a pharmaceutically acceptable salt thereof comprised in the pharmaceutical composition is in the form of a crystalline.

According to preferred embodiments of the present disclosure, the (R)-(+)-verapamil comprised in the pharmaceutical composition is in the form of hydrochloride salt.

Suitable examples of the α-glycosidase inhibitor for use in the pharmaceutical composition include, but are not limited to, acarbose, miglitose, and voglibose. In one preferred embodiment, the α-glycosidase inhibitor comprised in the pharmaceutical composition is acarbose.

According to preferred embodiments of the present disclosure, the pharmaceutical composition comprising (R)-(+)-verapamil or a pharmaceutically acceptable salt thereof and an α-glycosidase inhibitor is suitable for oral, intravenous, intramuscular, intraperitoneal, intracranial, subcutaneous, transmucosal, or intrarectal administration. In one preferred embodiment, the medicament is administered orally. The medicament suitable for oral administration may be provided as tablets, pills, granules, powders, solutions, suspensions, syrups or capsules.

According to preferred embodiments of the present disclosure, (R)-(+)-verapamil or a pharmaceutically acceptable salt thereof and α-glycosidase inhibitor are respectively present in the amount of 15 to 1,000 mg and 10 to 1,000 mg in the pharmaceutical composition.

Another aspect of the present invention relates to a method of treating hyperglycemia, such as type I, type II diabetes mellitus, gestational diabetes, other forms of diabetes and/or disorders related thereto. The method includes respectively administering to a subject suffering from diabetes mellitus and/or disorders related thereto, effective amounts of (R)-(+)-verapamil or a pharmaceutically acceptable salt thereof and an α-glycosidase inhibitor to alleviate or ameliorate the symptoms associated with diabetes mellitus.

Suitable examples of the α-glycosidase inhibitor for use in the pharmaceutical composition include, but are not limited to, acarbose, miglitose, and voglibose. In one preferred embodiment, the α-glycosidase inhibitor comprised in the pharmaceutical composition is acarbose.

According to preferred embodiments of the present disclosure, the (R)-(+)-verapamil or a pharmaceutically acceptable salt thereof is administered in the form of a crystalline.

According to preferred embodiments of the present disclosure, the (R)-(+)-verapamil is administered in the form of a hydrochloride salt.

According to embodiments of the present disclosure, the (R)-(+)-verapamil or a pharmaceutically acceptable salt thereof is administered in the amount from about 15 to 1,000 mg/day. Preferably, the (R)-(+)-verapamil or a pharmaceutically acceptable salt thereof is administered in the amount from about 25 to 800 mg/day. More preferably, the (R)-(+)-verapamil or a pharmaceutically acceptable salt thereof is administered in the amount from about 30 to 600 mg/day.

According to embodiments of the present disclosure, the α-glycosidase inhibitor is administered in the amount from about 10 to 1,000 mg/day. Preferably, the α-glycosidase inhibitor is administered in the amount from about 25 to 600 mg/day. More preferably, the α-glycosidase inhibitor is administered in the amount from about 75 to 300 mg/day.

According to embodiments of the present disclosure, the (R)-(+)-verapamil or a pharmaceutically acceptable salt thereof and the α-glycosidase inhibitor may be respectively administered orally, intravenously, intramuscularly, intraperitoneally, intracranially, subcutaneously, transmucosally, or intrarectally. In one preferred embodiment, the (R)-(+)-verapamil or a pharmaceutically acceptable salt thereof and the α~glycosidase inhibitor are respectively administered orally. The medicament suitable for oral administration may be provided as tablets, pills, granules, powders, solutions, suspensions, syrups or capsules.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
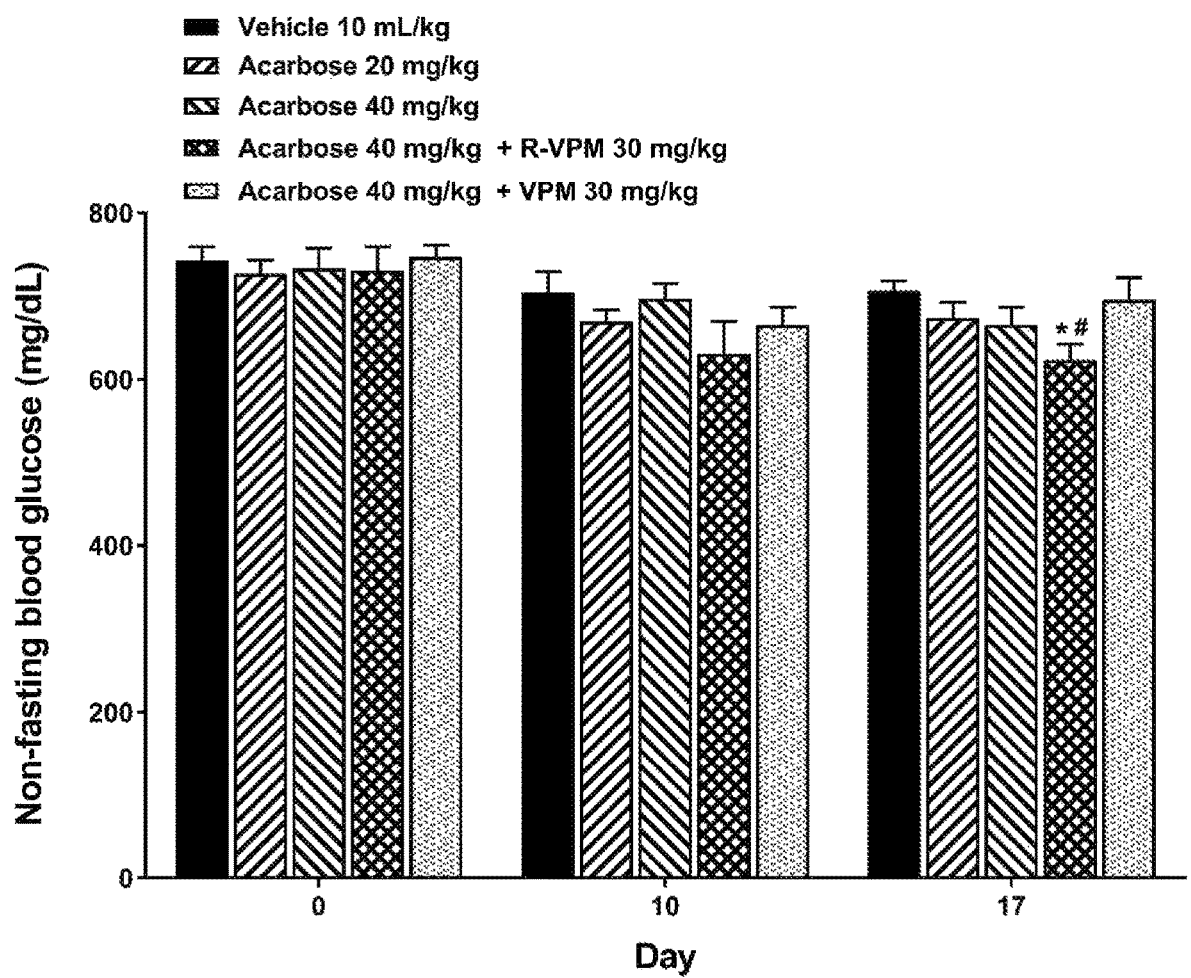
FIG. 1 is a bar graph illustrating the effects of acarbose alone and its combination with (R)-(+)-verapamil HCl or racemic verapamil HCl on the level of non-fasting blood glucose in NIDDM diabetic mice in accordance with Example 1 of this invention, in which differences are considered significant at *P<0.05, vs vehicle control by one-way ANOVA followed by Dunnett's test, and differences are considered significant at # P<0.05, vs vehicle control is performed using unpaired Student's t-test.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "diabetes mellitus" refers to type I, type II diabetes mellitus, gestational diabetes, and other forms of diabetes. Other forms diabetes may be latent autoimmune diabetes of adult (LADA), congenital diabetes, steroid diabetes, pancreatic defects related diabetes (e.g., chronic pancreatitis related diabetes, cystic fibrosis related diabetes, pancreatic neoplasia related diabetes, hemochromatosis related diabetes, and fibrocalculous pancreatopaty related diabetes), endocrinopathy related diabetes (e.g., acromegaly related diabetes, Crushing syndrome related diabetes, hyperthyroidism related diabetes, pheochromocytoma related diabetes, and glucagonoma related diabetes), infection related diabetes (e.g., cytomegalovirus infection related diabetes, and coxackievirus B related diabetes), diabetic angiopathy (e.g., diabetic retinopathy and diabetic nephropathy), and drug related diabetes (e.g., glucocorticoids related diabetes, thyroid hormone related diabetes, β-adrenergic agonists related diabetes, and statins related diabetes). Frequently correlated with type II diabetes mellitus are one or more of the metabolic syndrome, obesity, insulin resistance, dyslipidemia and a pathological glucose tolerance. Subjects with diabetes mellitus manifest varying degrees of increased blood pressure, increased levels of cholesterol and/or triglycerides, increased levels of uric acid and increased levels of factors that promote coagulation. Therefore, "disorders related to diabetes mellitus" as used herein refers to hypertension, hyperlipidemia, hyperuricemia, gout and hypercoagulability, i.e. an abnormal, increased tendency to form clots inside blood vessels. These disorders are well-recognized risk factors for atherosclerotic macrovascular as well as microvascular diseases. Atherosclerotic macrovascular diseases include myocardial infarction, stroke and limb amputation. Microvascular complications involve blindness, renal diseases and debilitating neuropathies.

The term "treatment" as used herein are intended to mean obtaining a desired pharmacological and/or physiologic effect, e.g., reducing blood glucose level in a hyperglycemia subject. The effect may be prophylactic in terms of completely or partially preventing a disease or symptom thereof and/or therapeutic in terms of a partial or complete cure for a disease and/or adverse effect attributable to the disease. "Treatment" as used herein includes, but is not limited to, preventative (e.g., prophylactic), curative or palliative treatment of a disease in a mammal, particularly human; and includes: (1) preventative (e.g., prophylactic), curative or palliative treatment of a disease or condition (e.g., diabetes mellitus or disorders related thereto) from occurring in an individual who may be pre-disposed to the disease but has not yet been diagnosed as having it; (2) inhibiting a disease (e.g., by promoting the proliferation of insulin-producing beta cells or suppressing apoptosis of these cells); or (3) relieving a disease (e.g., reducing symptoms associated with the disease).

The term "administered", "administering" or "administration" are used interchangeably herein to refer a mode of delivery, including, without limitation, orally, intravenously, intramuscularly, intraperitoneally, intraarterially, intracranially, transmucosally (e.g., inhalation, and intranasally), or subcutaneously administering of an agent (e.g., a compound or a composition) of the present invention. In preferred embodiments, the compound of the present disclosure (i.e., (R)-(+)-verapamil and α-glycosidase inhibitor) is formulated into compositions that are suitable for oral administration.

The term "an effective amount" as used herein refers to an amount effective, at dosages, and for periods of time necessary, to achieve the desired result with respect to the treatment of a disease resulted from hyperglycemia. For example, in the treatment of diabetes mellitus, an agent (i.e., the present compound) which decrease, prevents, delays or suppresses or arrests any symptoms related to diabetes mellitus would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) per day. The effective amount may be divided into one, two or more doses in a suitable form to be administered at one, two or more times throughout a designated time period.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "excipient" as used herein means any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The term "racemic" as used herein refers to a mixture of the (R)- and (S)-enantiomers, or stereoisomers, of verapamil, in which neither enantiomer or stereoisomer is substantially purified from the other.

II. Treatment of Diabetes Mellitus and Disorders Related thereto 2.1 Treatment Methods Verapamil (e.g., 2-(3,4-dimethoxyphenyl)-5-[2-(3,4-dimethoxyphenyl)ethyl-methylamino]-2-propan-2-ylpentanenitrile) is a known drug with various medicinal indications. Traditionally, it is used for treating coronary disease, such as hypertension. The compound has a stereogenic center, hence can be separated into its optical enantiomers. The (S)-enantiomer is known to possess the majority of the calcium channel antagonist activity, whereas the (R)-enantiomer is known to possess agonist activity toward somatostatin receptor 2, and antagonist activity toward orexin receptors 1 and 2, dopamine $D_{2L}$ receptor, sodium and calcium channels (see WO 2011/057471A1); accordingly, the (R)-enantiomer is useful as a medicament for treating diseases or conditions related to these receptors in a human subject.

The present invention in general, relates to the combined use of (R)-(+)-verapamil and an α-glycosidase inhibitor, in which the combination is capable of reducing both the non-fasting and the 6-hrs fasting blood glucose level in a diabetic subject. Accordingly, the (R)-(+)-verapamil and the α-glycosidase inhibitor, may be manufactured into a medicament for use in the treatment of diabetes mellitus and/or disorders related thereto.

In this regard, a particular aspect of the present invention relates to a method of treating a subject suffering from diabetes mellitus and/or disorders related thereto. The method includes the step of, administering to the subject an effective amount of (R)-(+)-verapamil or a pharmaceutically acceptable salt thereof (i.e., (R)-(+)-verapamil HCl) and an α-glycosidase inhibitor, so as to ameliorate or alleviate symptoms associated to diabetes mellitus and/or disorders related thereto.

(R)-(+)-verapamil may be obtained from racemic mixture of verapamil by high performance liquid chromatography (HPLC) separation or resolution of the enantiomers using any available means, such as optically active resolving acid. Alternatively, (R)-(+)-verapamil may be synthesized by stereospecific synthesis using any method known in the related art. Stereospecific synthesis in general can result in products with high enantiomeric purity. In cases when the enantiomeric purity is not sufficient, then the synthetic product may be subject to further purification process to enhance the enantiomeric purity by separating (R)-(+)-verapamil from (S)-(−)-verapamil. Examples of processes for resolving racemic verapamil to produce (R)-(+)-verapamil are well known to those of ordinary skill in the art.

According to some preferred embodiments, the (R)-(+)-verapamil or a pharmaceutically acceptable salt thereof is administered in a crystalline form. The crystalline of (R)-(+)-verapamil or a pharmaceutically acceptable salt thereof may be produced by any known crystallization method, e.g., saturation method. In one example, (R)-(+)-verapamil HCl is dissolved in suitable solvent(s), which include but are not limited to, ethyl acetate, toluene, and 1,4-dioxane/heptane (1:1), until a saturated solution is obtained; the saturated solution is then cooled to form (R)-(+)-verapamil HCl crystals therefrom.

According to preferred embodiments, the (R)-(+)-verapamil suitable for use in the present invention is in the form of hydrochloride salt, that is, (R)-(+)-verapamil HCl.

According to preferred embodiments, the (R)-(+)-verapamil or a pharmaceutically acceptable salt thereof is administered with an α-glycosidase inhibitor to ameliorate or alleviate the hyperglycemia state of the subject.

Suitable examples of the α-glycosidase inhibitor include, but are not limited to, acarbose, miglitose, and voglibose.

According to preferred embodiments of the present disclosure, (R)-(+)-verapamil HCl and acarbose are respectively administered to the subject to ameliorate or alleviate the hyperglycemia state of the subject.

According to embodiments of the present disclosure, (R)-(+)-verapamil or a pharmaceutically acceptable salt thereof may be administered to the subject in need of such treatment in the amount of 15 to 1,000 mg/day, such as 15, 20, 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000 mg/day; preferably, the (R)-(+)-verapamil or a pharmaceutically acceptable salt thereof is administered in the amount from about 25 to 800 mg/day, such as 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 mg/day; more preferably, the (R)-(+)-verapamil or a pharmaceutically acceptable salt thereof is administered in the amount from about 30 to 600 mg/day, such as 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600 mg/day.

According to embodiments of the present disclosure, the α-glycosidase inhibitor may be administered to the subject in need of such treatment in the amount of 10 to 1,000 mg/day, such as 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000 mg/day; preferably, the α-glycosidase inhibitor is administered in the amount from about 25 to 600 mg/day, such as 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, and 600 mg/day; more preferably, the α-glycosidase inhibitor is administered in the amount from about 75 to 300 mg/day, such as 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, and 300 mg/day.

According to preferred embodiments, (R)-(+)-verapamil or a pharmaceutically acceptable salt thereof is administered to a subject in need thereof along with acarbose, in which the combined treatment results in the reduction in the levels of non-fasting blood glucose as well as fasting blood glucose.

According to embodiments of the present disclosure, the (R)-(+)-verapamil or a pharmaceutically acceptable salt thereof, as well as the α-glycosidase inhibitor, may be respectively administered via any suitable route, which includes, but is not limited to, oral, intraveneous, intramuscular, intraperitoneal, intraarterial, intracranial, and subcutaneous route. In preferred embodiment, (R)-(+)-verapamil hydrochloride and the α-glycosidase inhibitor (e.g., acarbose) are orally administered to the subject in need thereof, respectively.

In further embodiment, the method is for the treatment of diabetes that responses poorly to oral hyperglycemia agent.

2.2 Pharmaceutical Compositions

A further aspect of the present invention relates to pharmaceutical compositions for the treatment of diabetes mellitus and/or disorders related thereto.

Some embodiments of the present disclosure aim at providing a pharmaceutical composition, which comprises (R)-(+)-verapamil or a pharmaceutically acceptable salt thereof; an α-glycosidase inhibitor; and a pharmaceutically acceptable excipient.

According to preferred embodiments of the present disclosure, the (R)-(+)-verapamil or a pharmaceutically acceptable salt thereof comprised in the pharmaceutical composition is in the form of a crystalline.

According to preferred embodiments of the present disclosure, the (R)-(+)-verapamil comprised in the pharmaceutical composition is in the form of hydrochloride salt.

Suitable examples of the α-glycosidase inhibitor for use in the pharmaceutical composition include, but are not limited to, acarbose, miglitose, and voglibose. In one preferred embodiment, the α-glycosidase inhibitor comprised in the pharmaceutical composition is acarbose.

To produce the pharmaceutical composition, suitable amounts of (R)-(+)-verapamil or a pharmaceutically acceptable salt thereof and the α-glycosidase inhibitor are mixed with suitable excipients and formulated into a dosage form suitable for administering orally, intraveneously, intramuscularly, intraperitoneally, intraarterially, intracranially, transmucosally (e.g., inhalation, buccal, and intranasally), or subcutaneously. Suitable excipients are known to those of skill in the art and described, for example, in Handbook of Pharmaceutical Excipients (Kibbe (ed.), $3^{rd}$ Edition (2000), American Pharmaceutical Association, Washington, D.C.), and Remington's Pharmaceutical Sciences (Gennaro (ed.), $20^{th}$ edition (2000), Mack Publishing Inc., Easton, Pa.), which for their disclosure relating to excipients and dosage forms, are incorporated herein by reference. For example, suitable excipients include, but are not limited to, starches, sugars, microcrystalline cellulose, diluents, granulating agents, lubricants, binders, disintegrating agents, wetting agents, lubricants, emulsifiers, coloring agent, release agents, coating agents, sweetening agents, flavoring agents, preservatives, plasticizers, gelling agents, thickeners, hardeners, setting agents, suspending agents, surfactants, humectants, carriers, stabilizers, antioxidants, and combinations thereof.

According to preferred embodiments of the present disclosure, the pharmaceutical composition is suitable for oral, intravenous, intramuscular, intraperitoneal, intracranial, subcutaneous, transmucosal, or intrarectal administration. In one preferred embodiment, the medicament is administered orally. The pharmaceutical composition suitable for oral administration may be provided as tablets, pills, granules, powders, solutions, suspensions, syrups or capsules.

In the case for oral administration, (R)-(+)-verapamil or a pharmaceutically acceptable salt thereof and the α-glycosidase inhibitor may be formulated into a dosage form that is a tablet, which may optionally be scored or prepared with coatings and shells, such as entering coatings, and coatings for modifying the rate of release. Further, any of the solid dosage form may be encapsulated in soft and hard gelatin capsules using any of the excipients known in the art.

(R)-(+)-verapamil or a pharmaceutically acceptable salt thereof and the α-glycosidase inhibitor may also be formulated into a liquid dosage form for oral administration. Suitable formulation include emulsion, solutions, suspension or syrup, it can be produced by conventional techniques using diluents commonly used in the art, such as water, glycerol esters, alcohols, vegetable oils, and etc. The liquid formulation may optionally include adjuvants such as wetting agents, emulsifying agents, and suspending agents, sweetening, flavoring, coloring, and preservative agents. The liquid formulation may also be filled into soft gelatin capsules. For example, the liquid may include a solution, suspension, emulsion, precipitate, or any other desired liquid media carrying the (R)-(+)-verapamil and the α-glycosidase inhibitor. The liquid may be designed to improve the solubility of the (R)-(+)-verapamil and the α-glycosidase inhibitor upon release, or may be designed to form a drug-containing emulsion or dispersed phase upon release. Examples of such techniques are well known in the related art. Soft gelatin capsules may be coated, as desired, with a functional coating, such as to delay the release of the drug.

In the case of parenteral administration, (R)-(+)-verapamil or a pharmaceutically acceptable salt thereof and the α-glycosidase inhibitor may be formulated into injectable forms for intravenous, subcutaneous or intramuscular administration. An injection can be prepared by dissolving the compound the present disclosure (e.g., (R)-(+)-verapamil or a pharmaceutically acceptable salt thereof, or acarbose) in water soluble solution such as physiological saline, or water insoluble solution consisting of organic esters such as propylene glycol, polyethylene glycol, or vegetable oils (e.g., sesame oil).

In the case of transdermal administration, for example, a dosage form as an ointment or a cream can be employed. The ointment can be produced by mixing the compound the present disclosure (e.g., (R)-(+)-verapamil or a pharmaceutically acceptable salt thereof; or acarbose) with fats or oils and etc; and the cream can be produced by mixing compound the present disclosure (e.g., (R)-(+)-verapamil or a pharmaceutically acceptable salt thereof; or acarbose) with emulsifiers. The transdermal formulation may be a liquid or a powdery formulation. In a liquid formulation water, salt solution, phosphate buffer, acetate buffer and etc may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and etc, and non-water absorbing materials such as cellulose, starches, gums, vegetable oils or cross-linked polymers. Further, antioxidants, colorants, preservatives may be added to the powdery formulation. The liquid or powdery formulation may be administered by use of a spray apparatus.

In the case of rectal administration, it may be in the form of suppository using a gelatin soft capsule.

In case of inhalation through nose or mouth, a solution or suspension containing the compounds the present disclosure (e.g., (R)-(+)-verapamil or a pharmaceutically acceptable salt thereof; and acarbose) and a pharmaceutical excipient generally accepted for this purpose is inhaled through an inhalant aerosol spray. Alternatively, the compounds the present disclosure (e.g., (R)-(+)-verapamil or a pharmaceutically acceptable salt thereof; and acarbose) in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

According to some preferred embodiments of the present disclosure, the present pharmaceutical composition is in the form of a tablet, which comprises 10 to 1,000 mg of (R)-(+)-verapamil or a pharmaceutically acceptable salt thereof, such as 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1,000 mg (R)-(+)-verapamil or a pharmaceutically acceptable salt thereof; 15 to 1,000 mg of acarbose, such as 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1,000 mg acarbose; and a pharmaceutically acceptable carrier. Preferably, the pharmaceutical composition comprises 25 to 800 mg of (R)-(+)-verapamil or a pharmaceutically acceptable salt thereof, such as 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 610, 620, 630, 640, 650, 660, 670, 680, 690, 700, 710, 720, 730, 740, 750, 760, 770, 780, 790, and 800 mg (R)-(+)-verapamil or a pharmaceutically acceptable salt thereof; 25 to 600 mg of acarbose, such as 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, and 600 mg acarbose; and a pharmaceutically acceptable carrier. In general, the present pharmaceutical composition is administered to the subject in single or divided doses 2, 3, 4 or more times each day. Alternatively, the dose may be delivered once every 2, 3, 4, 5 or more days. In one preferred embodiment, the pharmaceutical composition is administered twice per day.

The present invention will now be described in further detail with reference to the following examples. However, it should be understood that the present invention is not limited to the specified examples.

EXAMPLES

Materials and Methods
Materials.
(R)-(+)-verapamil HCl and racemic verapamil HCl were respectively provided by Center Laboratories Inc (Taipei, Taiwan, R.O.C.). Glucometer was purchased from Abbott (USA). Glucose assay kits were purchased form Denka Seiken Co. Ltd (Tokyo, Japan). Insulin and acarbose were both from Sigma-Aldrich (USA), and HbA1c assay kits were from Fujirebio (Japan).

Animals.
Wide-type male C57BL/6 mice (each weighted about 20-25 g), non-insulin dependent diabetic mellitus (NIDDM) male db/db mice (C57BLKS/J lar-+Lepr$^{db}$/+Lepr$^{db}$, each weighted about 45±10 g) were used in the present study.

C57BL/6 mice were provided by BioLASCO Taiwan (authorized by Charles River Laboratory, Wilmington, Mass.).

NIDDM mice were provided by Institute for Animal Reproduction (IAR, Japan). They exhibited hyperinsulinemia, hyperglycemia, and islet atrophy and were used at about 9-10 weeks of age. These animals were housed singly in Individually Ventilated cages Racks (IVC Racks, 36 Mini Isolator systems (Tecniplast, Italy) throughout the study.

All were maintained in the animal facility with controlled temperature (20-24° C.), humidity (50-80%) and a 12 h/12 h light/dark cycle (light on at 7:00 a.m.) with food and water provided ad libitum. Experimental procedures for handling the mice complied with relevant regulations set forth in "Guide for the Care and Use of Laboratory Animals: Eighth Edition" (National Academies Press, Washington, D.C., 2011) in AAALAC-accredited laboratory animal facility. (Eurofins Panlabs Taiwan, Ltd.)

NIDDM Mice and Treatment
NIDDM mice were acclimated at least one week and then grouped for treatment when the average blood glucose value was ≥250 mg/dl after 6-hr fasting. Test compounds (i.e., verapamil HCl in racemic form (VPM, bid), (R)-(+)-verapamil HCl (R-VPM, bid), acarbose (once daily, qd), or the combination of R-VPM (bid) and acarbose (qd) at the designated dose was orally fed to each mice from day 1, and continued for 16 consecutive days to day 17. Non-fasting blood glucose levels as well as 6-hr fasting blood glucose levels were measured on designated days. Specifically, 6-hr fasting blood glucose levels were measured on day −3 (before treatment), and days 7 and 14 (1 hr after acarbose and the $2^{nd}$ dosing of VPM or R-VPM), respectively. Blood glucose from non-fasting animals were measured on day 0 (before treatment), and days 10 and 17 (1 hr after acarbose and the $2^{nd}$ dosing of VPM or R-VPM). In addition, blood HbA1c was measured on day −3 and day 17. Body weight of each test animal was also measured during the study period.

Statistics
Results were expressed as the mean±standard error of the mean (SEM). Unpaired student's t-test or one-way ANOVA followed by Dunnett's test was used for statistical comparisons between substance-treated and vehicle-treated groups. Differences are considered significant at P<0.05.

Example 1 Combined Treatment of (R)-(+)-verapamil HCl and Acarbose Reduced Blood Glucose Level in NIDDM Mice In this example, the combined effects of acarbose and (R)-(+)-verapamil HCl (R-VPM) or racemic verapamil (VPM) on non-fasting and 6-hr fasting blood glucose were evaluated in NIDDM mice. Results are provided in FIGS. 1 and 2.

Referring to FIG. 1, which depicts the non-fasting blood glucose levels of NIDDM mice on days 0, 10, and 17 treated with acarbose (20 or 40 mg/Kg, qd) alone, or in combination with (R)-(+)-verapamil HCl (R-VPM, 30 mg/kg, bid) or racemic verapamil (VPM, 30 mg/Kg, bid). It was found that acarbose (20 or 40 mg/Kg, qd) alone only slightly reduced blood glucose levels on days 10 and 17; however, when the test animals were given both acarbose (40 mg/Kg, qd) and (R)-(+)-verapamil HCl (R-VPM, 30 mg/kg, bid), their non-fasting blood glucose levels were further reduced, as compared to those receiving acarbose alone. In addition, combined use of racemic verapamil and acarbose was ineffective in reducing the blood glucose level of NIDDM mice.

Figure 2:
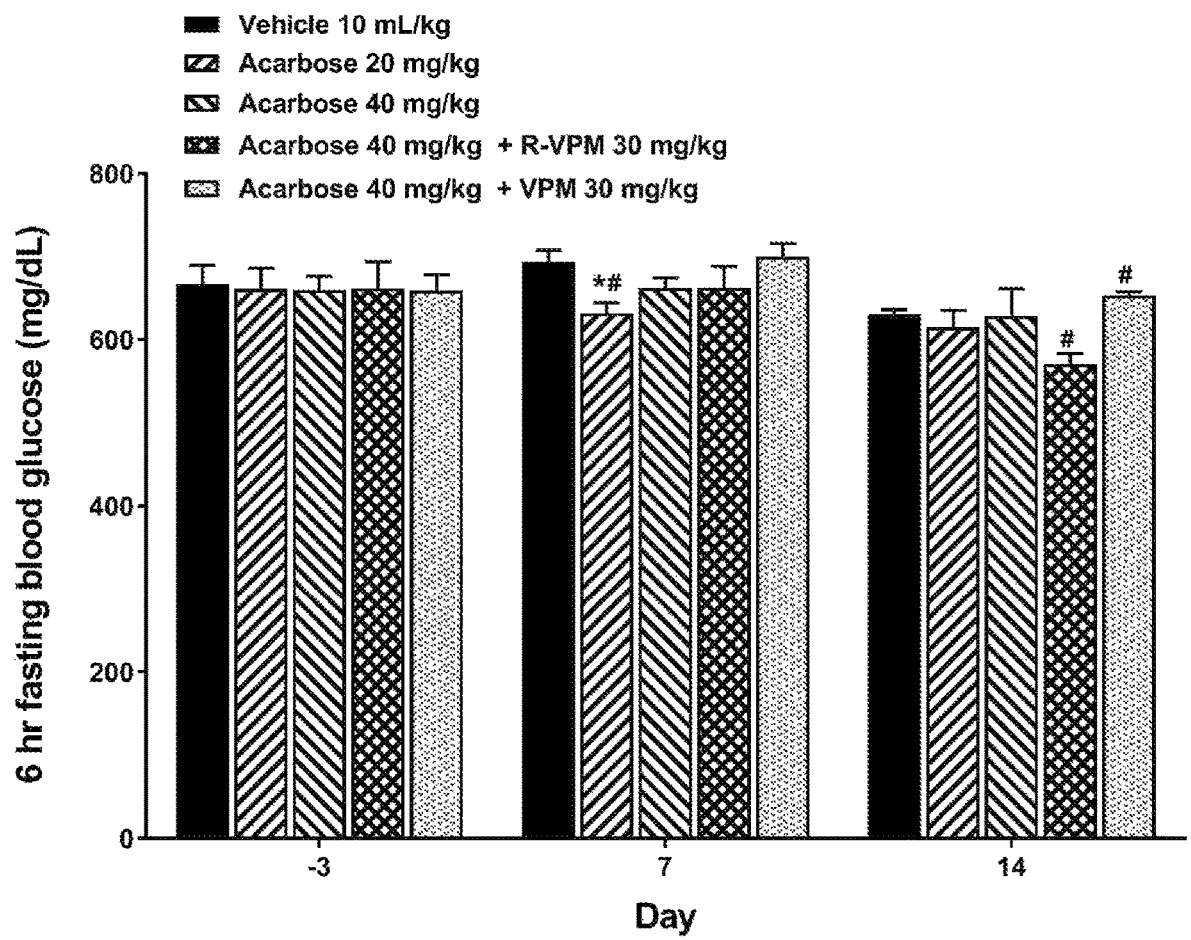
FIG. 2 is a bar graph illustrating the effects of acarbose alone and its combination with (R)-(+)-verapamil HCl or racemic verapamil HCl on the level of 6-hrs fasting blood glucose in NIDDM diabetic mice in accordance with Example 1 of this invention, in which differences are considered significant at *P<0.05, vs vehicle control by one-way ANOVA followed by Dunnett's test, and differences are considered significant at # P<0.05, vs vehicle control is performed using unpaired Student's t-test.

Similar effects of acarbose and/or its combination with (R)-(+)-verapamil were also found on the 6-hrs fasting blood glucose levels. As depicted in FIG. 2, the combined use of acarbose (40 mg/Kg, qd) and (R)-(+)-verapamil (30 mg/Kg, bid) effectively reduced the 6-hrs fasting blood glucose levels of NIDDM mice on day 14, while the combined use of acarbose (40 mg/Kg, qd) and racemic verapamil resulted in even worst effect on the 6-hrs fasting blood glucose level, instead of a reduction, the 6-hrs fasting blood glucose level was increased, as compared to that of the vehicle control.

Another common indicator, glycated haemolglobin (HbA1c), which reflects average blood glucose levels over a duration was also measured in the present study. HbA1c develops when haemolglobin, a protein within red blood cells that carries oxygen throughout the body joins with glucose in the blood and becomes "glycated." Since red blood cells in a human body survive for about 8-12 weeks before renewal, thus, the level of HbA1c gives an overall picture of average blood sugar levels over such period. It was found that oral administrations of acarbose alone (20 or 40 mg/Kg) and/or its combination with (R)-(+)-verapamil or racemic verapamil for 17 consecutive days had minimum or no effect on HbA1c level, as compared with that of the control animals (data not shown).

Taken together the findings in the working examples, acarbose alone (20 or 40 mg/Kg, qd) may only slightly reduce non-fasting blood glucose level, however, the combined use of acarbose (40 mg/Kg, qd) and (R)-(+)-verapamil (30 mg/Kg, bid) produces significant reduction in non-fasting blood glucose level, as well as in the level of 6-hrs fasting blood glucose level. Accordingly, acarbose and (R)-(+)-verapamil may be suitable for use as a medicament for treating diabetes mellitus and/or disorders related thereto.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject having diabetes mellitus and/or disorders related to diabetes mellitus comprising administering to the subject an effective amount of (R)-(+)-verapamil or a pharmaceutically acceptable salt thereof and acarbose, so as to reduce the blood glucose level of the subject.

2. The method of claim 1, wherein the (R)-(+)-verapamil or a pharmaceutically acceptable salt thereof is administered to the subject in the amount of 15 to 1,000 mg/day; and the acarbose is administered to the subject in the amount of 10 to 1,000 mg/day.

3. The method of claim 2, wherein the (R)-(+)-verapamil or a pharmaceutically acceptable salt thereof is administered to the subject in the amount of 25 to 800 mg/day; and the acarbose is administered to the subject in the amount of 25 to 600 mg/day.

4. The method of claim 1, wherein the (R)-(+)-verapamil or a pharmaceutically acceptable salt thereof is administered to the subject in single or divided doses 2 or 3 times each day; while the acarbose is administered to the subject in single or divided doses 2 or 3 times each day.

5. A pharmaceutical composition for the treatment of diabetes mellitus and/or disorders related to diabetes mellitus comprising, (R)-(+)-verapamil or a pharmaceutically acceptable salt thereof, acarbose, and a pharmaceutically acceptable excipient.

6. The pharmaceutical composition of claim 5, wherein the (R)-(+)-verapamil or a pharmaceutically acceptable salt thereof is present in the pharmaceutical composition in the amount of 15 to 1,000 mg; and the acarbose is present in the pharmaceutical composition in the amount of 10 to 1,000 mg.

7. The pharmaceutical composition of claim 6, wherein the (R)-(+)-verapamil or a pharmaceutically acceptable salt thereof is a is present in the pharmaceutical composition in the amount of 25 to 800 mg; and the acarbose is present in the pharmaceutical composition in the amount of 25 to 600 mg.

8. The pharmaceutical composition of claim 5, which is administered to the subject in single or divided doses 2 or 3 times each day.

* * * * *